United States Patent
Pollins, Sr.

(10) Patent No.: US 6,458,117 B1
(45) Date of Patent: Oct. 1, 2002

(54) INTRAOSSEOUS INFUSION ASSEMBLY AND METHOD FOR INTRAOSSEOUS INFUSION

(76) Inventor: Kevin Daniel Pollins, Sr., 7821 Hillcrest, Westland, MI (US) 48185

( * ) Notice: Subject to any disclaimer, the term of this patent is extended or adjusted under 35 U.S.C. 154(b) by 0 days.

(21) Appl. No.: 09/487,652

(22) Filed: Jan. 19, 2000

(51) Int. Cl.[7] ............................................. A61M 25/00
(52) U.S. Cl. .................... 604/523; 604/164.01; 606/92; 606/93; 606/94
(58) Field of Search ....................... 604/164.01, 164.06, 604/164.07, 523, 264, 93.01; 606/92, 93, 94, 167, 170, 184, 185

(56) References Cited

U.S. PATENT DOCUMENTS

| | | | | |
|---|---|---|---|---|
| 4,403,617 A | * | 9/1983 | Tretinyak | 604/164.01 |
| 4,631,051 A | * | 12/1986 | Harris | 604/164.01 |
| 4,792,328 A | * | 12/1988 | Beck et al. | 604/164.06 |
| 4,969,870 A | | 11/1990 | Kramer et al. | |
| 5,071,410 A | * | 12/1991 | Pazell | 604/164.01 |
| 5,152,749 A | * | 10/1992 | Giesy et al. | 604/164.01 |
| 5,372,583 A | | 12/1994 | Roberts et al. | |
| 5,713,874 A | * | 2/1998 | Ferber | 604/164.01 |
| 5,779,708 A | * | 7/1998 | Wu | 604/164.01 |
| 5,868,684 A | * | 2/1999 | Akerfeldt et al. | 604/264 |
| 5,997,504 A | * | 12/1999 | Bell | 604/93 |
| 6,135,769 A | * | 10/2000 | Kwan | 604/164.01 |
| 6,217,558 B1 | * | 4/2001 | Zadini et al. | 604/264 |
| 6,273,861 B1 | * | 8/2001 | Bates et al. | 604/164.01 |
| 6,319,230 B1 | * | 11/2001 | Palasis et al. | 604/164.01 |

* cited by examiner

*Primary Examiner*—Teresa Walberg
*Assistant Examiner*—Fadi H. Dahbour
(74) *Attorney, Agent, or Firm*—Law Offices of John Chupa and Associates, P.C.

(57) ABSTRACT

An intraosseous infusion assembly 10 including a first threaded member which is placed upon a bodily member 12 and above a bone 14 to which fluid 64 is to be communicated. The assembly 10 further includes a second member 20 which is received within the first member 16 and which includes a first generally hollow needle 32 which penetrates the bone 14 as the member 20 is received within the member 16. The assembly 10 further includes a third generally hollow member 28 which is selectively connected to a source 62 of the fluid 64. The assembly 10 also includes a fourth member 40 having a second and generally hollow needle 50 which is received within the first needle 32 and which penetrates the bone 14. The fluid 64 is communicated to the needle 50 by the member 28 and the fluid 64 is communicated to the bone 14 by the needle 50.

10 Claims, 2 Drawing Sheets

INTRAOSSEOUS INFUSION ASSEMBLY AND METHOD FOR INTRAOSSEOUS INFUSION

FIELD OF THE INVENTION

This invention relates to an infusion assembly which is selectively inserted into a bone and more particularly, to an intraosseous infusion assembly which allows liquids to be selectively infused or communicated into the marrow or traecula portion of a bone while reducing the likelihood that the assembly will traverse or pass through the bone and concomitantly reducing the likelihood that the assembly will be dislodged from the bone. This invention also relates to a method for using such an intraosseous assembly.

BACKGROUND OF THE INVENTION

Drugs and other types of liquids or fluids are typically delivered to a patient by use of a needle or catheter which is typically and selectively inserted within the vascular system of the patient. The vascular system then communicates the received liquids or fluids throughout the patient's body. While this arrangement does, in many cases, allow for the efficient and desirable transportation of the liquid or fluid into the patient's body, its use is dependent upon the ability to place the catheter within the various peripheral blood vessels contained within the patient's vascular system and the ability of these blood vessels to transport the received fluids throughout the patient's body.

Frequently, these peripheral blood vessels collapse due to a relatively serious circulatory shock and hemorrhaging, thereby causing these peripheral blood vessels to be substantially inaccessible and/or substantially hindering or preventing these peripheral blood vessels from transporting the fluids within the body. Such a collapse may alternatively increase the difficulty in locating and/or utilizing these peripheral blood vessels to transport these fluids, thereby undesirably increasing the amount of time necessary to provide infusions of fluid within a patient. Moreover, use of such peripheral blood vessels is relatively difficult in pediatric patients since these pediatric type blood vessels are relatively small.

When the peripheral blood vessels are inaccessible or difficult to utilize, an intraosseous type of needle is typically inserted into the trabecula portion and/or aspirating marrow portion of a bone. Typically such intraosseous needles are placed within the sternum or within a bone which resides within a leg and which is near the surface of the skin. The intraosseous needle is typically and communicatively coupled to a source of desired fluid and causes the fluid to be communicated to the trabecula or marrow where it is distributed within the patient's body.

While such intraosseous type needles and needle assemblies do allow such fluid to be desirably transported within a bone, they suffer from some drawbacks. That is, these needles oftentime traverse or extend through a bone since it is relatively difficult to determine the correct distance that these needles are to be placed within the bone and it is relatively difficult to determine the current position of the needle within the bone. The traversal of these needles through a bone causes discomfort and further injury to the patient as well as undesirable delaying the receipt of the fluid by the patient due to the need to attempt proper penetration of another bone. In many cases, such delays may cause death or irreparable injury to the patient.

Moreover, the placement of these intraosseous needles within a bone is "unstable" and the intraosseous needles tend to become dislodged from the bone, thereby causing an undesirable interruption of fluid transport, and endangering the life of the patient and causing further pain, discomfort, and potential injury to the patient.

There is therefore a need for a new and improved intraosseous needle and needle assembly which overcomes some or all of the previously delineated drawbacks of prior intraosseous needles and needle assemblies, There is therefore a further need for a method for intraosseously infusing fluid into a patient which overcomes some or all of the previously delineated drawbacks of prior infusion methodologies.

SUMMARY OF THE INVENTION

It is a first object of the present invention to provide an intraosseous infusion assembly which overcomes some or all of the previously delineated drawbacks of prior intraosseous assemblies.

It is a second object of the present invention to provide a methodology for infusing fluids into patients which overcomes some or all of the previously delineated infusion methodologies.

According to a first aspect of the present invention an intraosseous infusion assembly is provided for use with a bone containing member. The intraosseous infusion assembly includes a first threaded member; a second threaded member which is selectively inserted into the first threaded member and which includes a first needle which penetrates the bone as the second threaded member is selectively inserted into the first threaded member; a third member which is selectively inserted into the second member; and a top member which frictionally and removably receives the third member, the top member having a second needle which is selectively inserted into the reception member, the first needle, and the bone.

According to a second aspect of the present invention, a method for intraosseously transporting fluid to an individual of the type having at least one bone is provided. The method includes the steps of placing a first needle into the bone; and placing a second needle through the first needle and into the bone.

These and other features, aspects, and advantages of the present invention will become apparent from a reading of the following detailed description of the preferred embodiment of the invention and by reference to the following drawings.

DETAILED DESCRIPTION OF THE PREFERRED EMBODIMENT OF THE INVENTION

Figure 1:
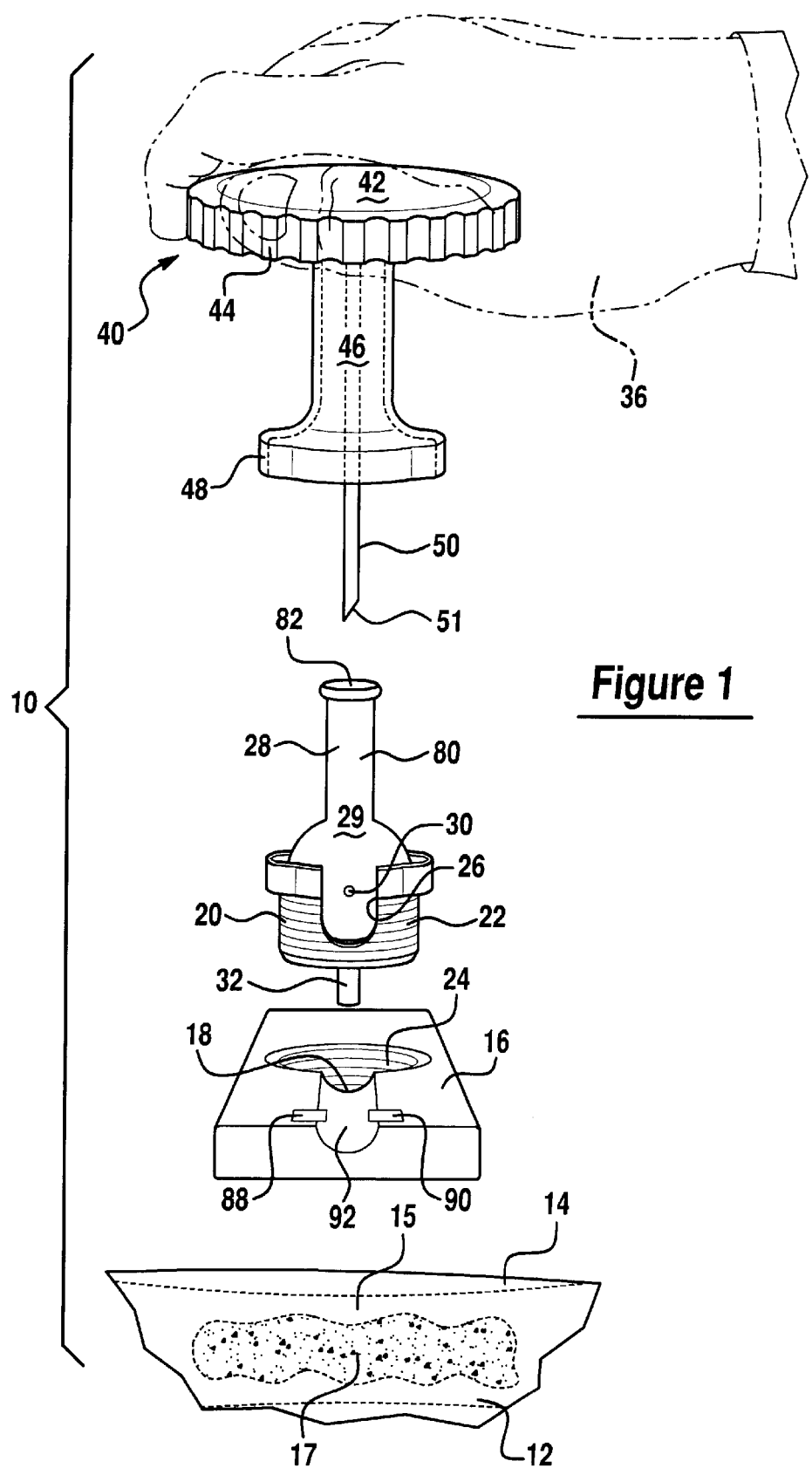
FIG. 1 is an unassembled perspective view of an intraosseous infusion assembly which is made in accordance with the teachings of the preferred embodiment of the invention.
Figure 2:
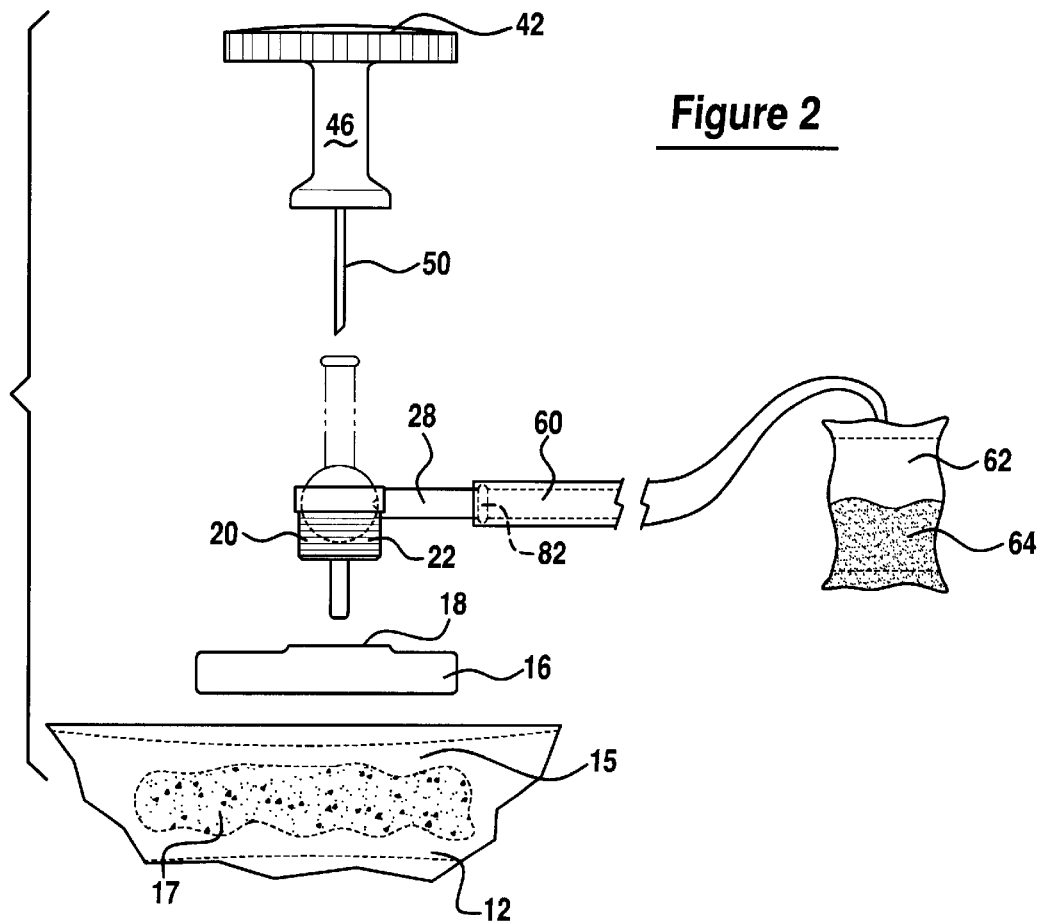
FIG. 2 is an unassembled side view of the intraosseous infusion assembly which is shown in FIG. 1 and which further illustrates the selective coupling of the intraosseous infusion assembly to a source of fluid.
Figure 3:
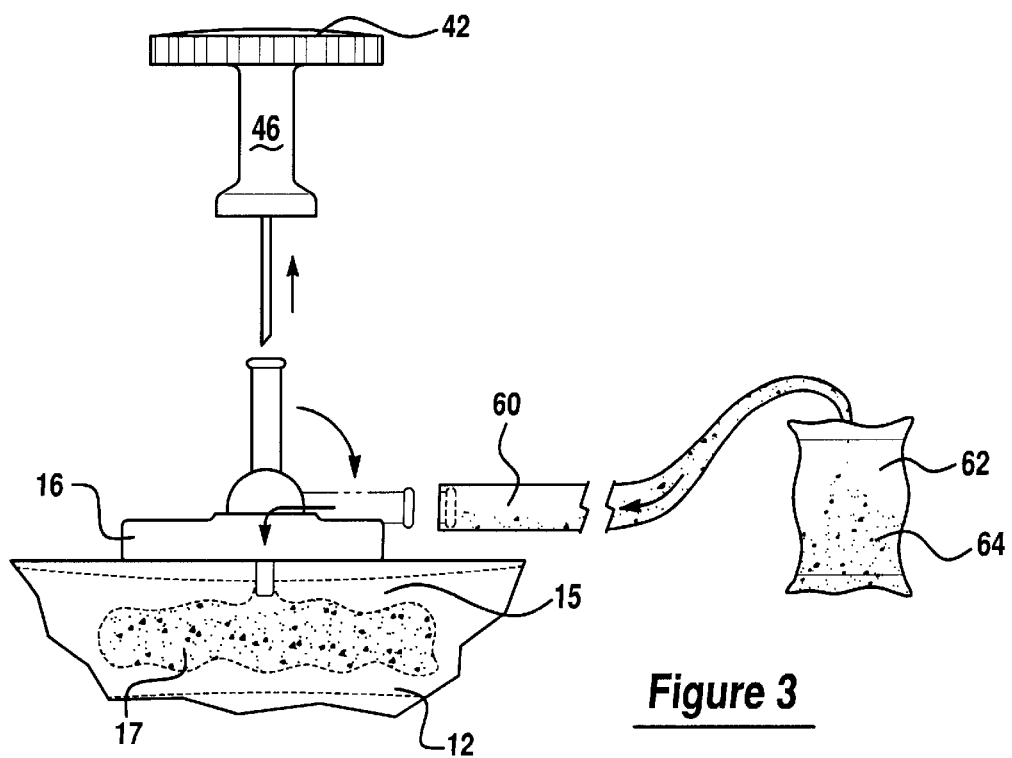
FIG. 3 is a side assembled view of the intraosseous infusion assembly which is shown in FIGS. 1 and 2 and illustrating the operative placement of the intraosseous infusion assembly within a bone.

Referring now to FIGS. 1–3, there is shown an intraosseous infusion assembly 10 which is made in accordance with the teachings of the preferred embodiment of the invention for use in combination with a bodily member 12, such a leg, arm, pelvis or sternum containing at least one bone 14. As shown, assembly 10 includes a first generally planar member 16 having a threaded and generally round cavity 18 which extends through the member 16. As shown best in FIG. 3, member 16 is adapted to rest upon the member 12 and to provide a secure and generally flat mounting surface for the remaining portions of assembly 10. Moreover, cavity 18 is selectively placed above the bone 14 which is to be penetrated by assembly 10.

Assembly 10 further includes a second and generally round and threaded member 20 which has a shape and a size which generally conforms to the size and shape of cavity 18. Particularly, threads 22 upon member 20 are complementary to threads 24 which are contained within or bound cavity 18. Hence, threads 22 and 24 cooperate to allow the member 20 to be selectively, removably, and firmly secured within the cavity 18. Member 20 further includes a slot 26 and a generally hollow member 28 forming a cavity 29 and at least one orifice and/or orifice containing protrusion 30 which communicates with cavity 29. Herein after, the term "[1]protrusion 30" may refer either to an orifice or a protrusion containing an orifice which communicates with cavity 29. Member 28 is, in one non-limiting embodiment, movably secured within member 20 by conventional fasteners or adhesives, or may be frictionally and movably secured within the member 20. In the preferred embodiment of the invention, protrusion 30 is received within the slot 26. Member 28 further includes a generally hollow needle 32 which communicates with the cavity 29 and which extends through member 20. A itematively, needle 32 may be removably secured within another protrusion 30. Thus, as member 20 is inserted within cavity 18, needle 32 penetrates the bone matrix 15 of bone 14 and enters marrow 17. The length of needle 32 is relatively short, thereby substantially preventing the needle 32 from traversing through bone 14 even if bone 14 comprising a thin pediatric bone. Different members 20 having different lengths of needles 32 may be used in order to address the needs of different patients (e.g. smaller needles are used for pediatric patients), thereby increasing the overall utility of the assembly 10.

Assembly 10 further includes a top member 40 having a handle portion 42 with a serrated edge 44. Portion 42 is adapted to be held by a human hand 36 and to allow the top member 40 to be attached to members 28 and 20 in the manner which is more fully described below.

Member 40 further includes a generally hollow elongated portion 46 which, in one non-limiting embodiment, is integrally formed with portion 42 and which have a flared end 48. Further, member 40 includes a relatively long, solid needle 50 having a tapered end 51 which extends through member 46 and which is attached to portion 42.

The protruding threads 22 of member 20 are "threaded into" member 16. In operation, members 20 and 28 are placed within the hollow member 46. In one embodiment, some of the threads 22 protrude from flared end 48. In this manner, needle 50 is received within cavity 29 and within needle 32 and extends/protrudes from the needle 32. Needles 32 and 50 penetrate the bone 14. The placement of needle 50 within the needle 32 causes the relatively long needle 50 to be securely retained within the bone 14 and reduces the likelihood of breakage as the needle 32, 50 penetrate the bone 14. The placement of member 28 within portion 46 and the substantial encapsulation of members 20 and 28 by members 40 and members 16 further provides greater stability to the intraosseous infusion assembly 10, thereby reducing the likelihood that needles 32, 50 will become dislodged from bone 14.

After the insertion is completed, member 40 is removed form member 20. Then, neck portion 80 of member 28 is placed within slot 26 causing protrusion 30 to communicate with the hollow needle 32. Particularly the neck portion 80 is secured within channel 92 by flexible detant portions 88, 90.

As shown best in FIGS. 2 and 3, a tube 60 which is connected to a reservoir 62 of fluid 64 may be connected to the end 82, (i.e. end 82 may be frictionally received into the tubes 60), effective to allow the fluid 64 to be communicated to the cavity 29 and into the needle 50, thereby allowing the fluid 64 to enter the bone 14.

It is to be understood that the invention is not limited to the exact construction and method which has been described above, but that various changes and modifications may be made without departing from the spirit and the scope of the inventions as is more fully delineated in the following claims.

What is claimed is:

1. An intraosseous infusion assembly comprising a first member:
    a second member having a first needle, said second member further having at least one slot; and
    a third member having a second needle, said third member further having at least one orifice which communicates with said at least one slot.

2. The intraosseous infusion assembly of claim 1 wherein said first member includes a threaded cavity of a certain shape.

3. The intraosseous infusion assembly of claim 2 wherein said second member has a shape which is substantially similar to said certain shape.

4. The intraosseous infusion assembly of claim 3 wherein said second member is threaded.

5. The intraosseous infusion assembly of claim 3 wherein said certain shape is generally round.

6. The intraosseous infusion assembly of claim 1 wherein said second needle has a tapered end.

7. The intraosseous infusion assembly of claim 6 wherein said second needle is longer than said first needle.

8. The intraosseous infusion assembly of claim 1 wherein said first member is generally flat.

9. The intraosseous infusion assembly of claim 1 wherein said third member has a round top portion with serrated edge.

10. The intraosseous infusion assembly of claim 1 further comprising a reservoir of liquid which is communicatively coupled to said second member through said communicating at least one slot and said at least one orifice.

* * * * *